(12) United States Patent
Rosner et al.

(10) Patent No.: US 6,890,098 B2
(45) Date of Patent: May 10, 2005

(54) METHOD FOR CALIBRATING THE INTENSITY PROFILE FOR A MOVABLE X-RAY SOURCE

(75) Inventors: S. Jeffrey Rosner, Palo Alto, CA (US); Russell Iimura, Sunnyvale, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 168 days.

(21) Appl. No.: 10/302,507

(22) Filed: Nov. 22, 2002

(65) Prior Publication Data

US 2004/0101091 A1 May 27, 2004

(51) Int. Cl.$^7$ ................................................ H05G 1/02
(52) U.S. Cl. ...................... 378/196; 378/98.8; 378/207
(58) Field of Search ............................ 378/196, 98.8, 378/19, 207; 250/370.09, 370.11

(56) References Cited

U.S. PATENT DOCUMENTS

| | | | |
|---|---|---|---|
| 6,208,710 B1 | | 3/2001 | Nagai |
| 6,404,854 B1 | * | 6/2002 | Carroll et al. ............. 378/98.8 |
| 6,448,561 B1 | * | 9/2002 | Kaifu .................... 250/370.09 |
| 2002/0025022 A1 | * | 2/2002 | Kaifu et al. .................. 378/97 |
| 2003/0042425 A1 | * | 3/2003 | Tashiro et al. ......... 250/370.11 |
| 2003/0086523 A1 | * | 5/2003 | Tashiro et al. ................ 378/19 |

FOREIGN PATENT DOCUMENTS

| | | |
|---|---|---|
| EP | 0 948 930 A1 | 10/1999 |
| WO | WO 97/12232 | 9/1996 |

OTHER PUBLICATIONS

Hammersley, A.P. et al. "Calibration and Correction of Distortions in Two–Dimensional Detector Systems" American Institute of Physics, Mar. 1995, pp. 2729–2733.

* cited by examiner

Primary Examiner—Craig E. Church
Assistant Examiner—Irakli Kiknadze

(57) ABSTRACT

An imaging system and method for using the same is disclosed. The imaging system includes an x-ray detection array or plurality of detection arrays, a point x-ray source, and a controller. The point x-ray source moves relative to a detection array, each of the x-ray detectors subtending a solid angle at the point source that depends on the relative position of the point source and the detection array and on the location of the detector in the detection array. The signal generated by each x-ray detector depends on a calibration parameter that is independent of the solid angle subtended by that x-ray detector at the point source. The controller stores a table of calibration values that determines the calibration parameter for each of the x-ray detectors. The controller corrects the signals generated by the x-ray detectors for solid angle and for variations in the calibration parameter.

9 Claims, 3 Drawing Sheets

METHOD FOR CALIBRATING THE INTENSITY PROFILE FOR A MOVABLE X-RAY SOURCE

FIELD OF THE INVENTION

The present invention relates to x-ray imaging systems, and more particularly, to x-ray imaging systems in which the x-ray source moves relative to an x-ray detector.

BACKGROUND OF THE INVENTION

In a projection x-ray imaging system, the object to be imaged is placed between an x-ray source that is typically a point source and an array of x-ray detectors. When such arrays are densely packed, the individual detectors are referred to as pixels. In general, the point illumination source generates an x-ray field that is roughly isotropic. That is, the number of x-rays that are generated per unit solid angle at the source is roughly constant. The array of detectors is typically flat, and hence, the solid angle subtended by each detector varies across the array, since the various detectors have different distances and orientations relative to the source. For example, consider a system in which the source is located over the center of the detector array and oriented such that the center detector in the array is oriented at right angles with respect to the ray from the center of the detector to the source. The solid angle subtended by the detectors varies with the detector's distance from the center of the array. The detectors that are nearer the edge of the array, and hence, far from the center, receive a lower x-ray intensity than those nearer the center.

Ideally, the projection image formed by the array when an object is placed between the x-ray source and the array reflects the variations in x-ray absorption or scattering by the object without illumination artifacts. However, the above-described illumination variation in x-ray intensity generates artifacts, since an object that has a uniform absorbency across the object would appear to have a density that varies with position if the image is not corrected for the intensity variation.

In addition to the illumination variation discussed above, the image must be corrected for variations in the gain and offset of the various x-ray detectors in the array. The image sensors used in these systems are generally imperfect. Both the dark current and gain varies from pixel to pixel in the array. This variation is often called the "fixed pattern noise" or FPN. This variation is typically corrected by taking dark field (illumination off) and bright field (illumination on) images and creating a gain and offset value for each pixel. A table of these parameters is stored in a memory. These values are used to correct each pixel value prior to sending that pixel to the image user. It should be noted that this correction process also automatically calibrates the illumination variation discussed above as well.

If the relative position of the x-ray source and the detector array is fixed, such a lookup table correction procedure provides a viable method for correcting the image. However, in systems in which a large number of images are taken with different orientations between the x-ray source and the detector array, this procedure becomes impractical because a table of correction values must be stored for each possible orientation.

SUMMARY OF THE INVENTION

The present invention is an imaging system and method for using the same. The imaging system includes an x-ray detection array, a point x-ray source, and a controller. The x-ray detection array includes a plurality of x-ray detectors, each x-ray detector generating a signal indicative of the x-ray energy absorbed by the x-ray detector and is located at a unique location in the detection array. The point x-ray source moves relative to a detection array, each of the x-ray detectors subtending a solid angle at the point source that depends on the relative position of the point source and the detection array and on the location of the detector in the detection array. The signal generated by each x-ray detector depends on a calibration parameter that is independent of the solid angle subtended by that x-ray detector at the point source. The controller includes a memory that stores a table of calibration values that determines the calibration parameter for each of the x-ray detectors. The controller corrects the signals generated by the x-ray detectors for variations in the solid angle subtended by each of the x-ray detectors and for variations in the calibration parameter. The controller may also include a processor that determines the calibration values by measuring the signal from each of the x-ray detectors for two different relative positions of the x-ray source and the detection array. The calibration parameter typically defines the gain of the x-ray detector or an offset value for that x-ray detector. The controller may utilize a pipelined processor for correcting the signal generated by the x-ray detectors as the signals are read-out of the x-ray detection array.

DETAILED DESCRIPTION OF THE PREFERRED EMBODIMENTS OF THE INVENTION

Figure 1:
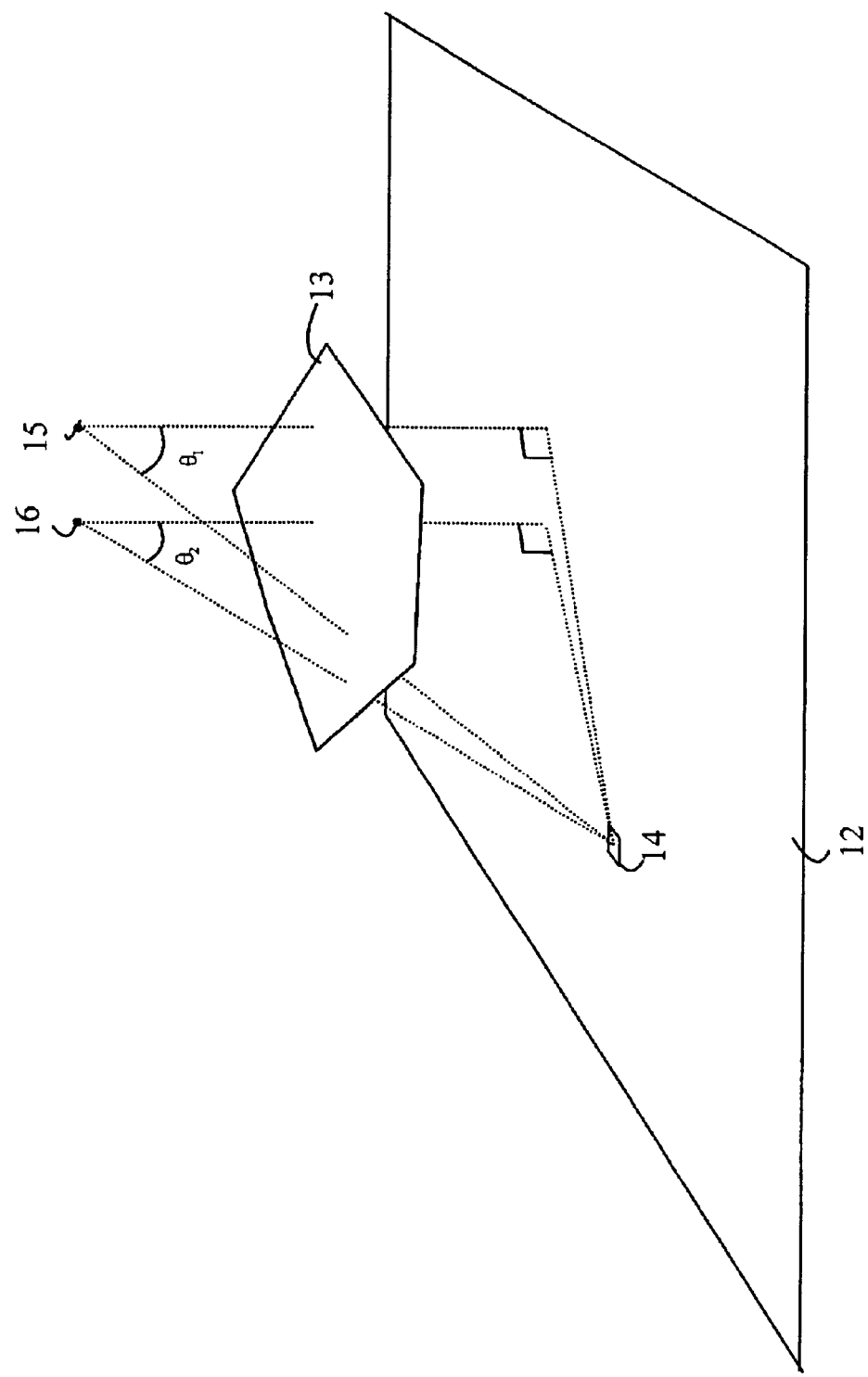
FIG. 1 illustrates the illumination of pixels in an image array 12 when an object 13 is illuminated from two different x-ray point sources.

The manner in which the present invention provides its advantages can be more easily understood with reference to FIG. 1 which illustrates the illumination of pixels in an detector array 12 when an object 13 is illuminated from two different x-ray point sources that are shown at 15 and 16. A typical pixel in the detector array is shown at 14. For the purposes of this discussion, it will be assumed that each of the pixels has the same area. It will also be assumed that the illumination generated by the source is independent of the source position. Denote the illumination intensity at the source by $I_1$ photons per steradian. In the absence of object 13, the signal $^0S_k$ generated by a pixel such as pixel 14 when the source is located at position 15 is given by:

$$^0S_k = G_k * I_i * \cos^4\theta_1 + F_k \quad (1)$$

Here, k denotes the $k^{th}$ pixel in the array; $G_k$ is a gain constant associated with the $k^{th}$ pixel, and $F_k$ is an offset constant associated with the $k^{th}$ pixel. It should be noted that $G_k$ and $F_k$ are independent of θ. Hence, if $^0S_k$ is measured for at least two different values of θ when object 13 is absent, the constants $G_k$ and $F_k$ can be determined for each of the pixels in the array.

When object 13 is inserted into the path of the x-rays, $I_1$ is reduced by an amount $A_k$ for the $k^{th}$ pixel. Here, $A_k$ is the absorbency of the object along the paths connecting the source and the pixel. That is, the signal form the $k^{th}$ pixel when the source is at $\theta_1$ and object 13 is in place is given by:

$$S_k = G_k * I_j * A_k * \cos^4\theta_1 + F_k \quad (2)$$

An x-ray image is constructed by displaying values related to $A_k$. Hence, the imaging system must solve Eq. (2) for the $A_k$ values.

While a single such image can be useful, data derived from a plurality of such images taken from with different orientations of the x-ray source relative to the object being imaged are often needed to provide sufficient data to reconstruct some detail of interest in the object. Most objects of interest are three-dimensional. The absorbency measured by a pixel is the sum of the absorbencies of all of the volume elements ("voxels") along the path between the x-ray source and the pixel. If the absorbency of one of these voxels is much greater than that of the other voxels along the path, this "dark" voxel can mask the values of the other voxels. By utilizing a number of different orientations of the source, the other voxels can be viewed without this interference in at least one of the alternative views. Accordingly, x-ray inspection systems and three-dimensional image reconstructed systems preferably utilize a number of different images taken at different source-object orientations.

As noted above, prior art systems operate by storing a table of values, the most common having two entries per pixel for a linear FPN correction, although some nonlinear sensors have coefficients of higher order polynomials or other descriptions. In the simplest linear case, the first entry specifies $G_k * \cos^4\theta$, and the second entry specifies $F_k$. Hence, the prior art systems must store a minimum of 2N entries for each possible value of $\theta$, where N is the number of pixels in the detector array. To avoid having to store one table of this form for each of a number of different $\theta$ values, prior art systems with a variable geometry arrange the x-ray hardware such that $\theta$ remains the same for all source positions when more than one source position is utilized as in, for example, analog laminography. More typically, however, a fixed imaging system is used, where the detector and the source are rigidly connected and move together to provide relative rotational and translational motion between the imaging system and object. Such arrangements, while reducing the data storage problem, markedly increase the cost of the hardware, and more importantly, limit the flexibility and throughput of an inspection system utilizing this type of design.

An imaging system according to the present invention preferably utilizes a scanning x-ray source or an array of small economical fixed sources and a detector array that does not move when the point source position changes. Since scanning x-ray sources are known to the art, a detailed description of such sources will not be presented here. For the purposes of this discussion, it is sufficient to note that a scanning x-ray source is a variant of the common cathode-ray tube that includes an electron gun that directs a beam of electrons onto a target. The position of impact of the electrons on the target is determined by a deflection system that moves the beam in response to one or more control signals. By moving the position of impact, the position of the x-ray source may be moved relative to the object being imaged without any form of mechanical motion. While the position of the x-ray target relative to the detector array may be fixed, the position of the x-ray source with respect to the detector array varies with the position on the target that is currently being bombarded with electrons.

Figure 2:
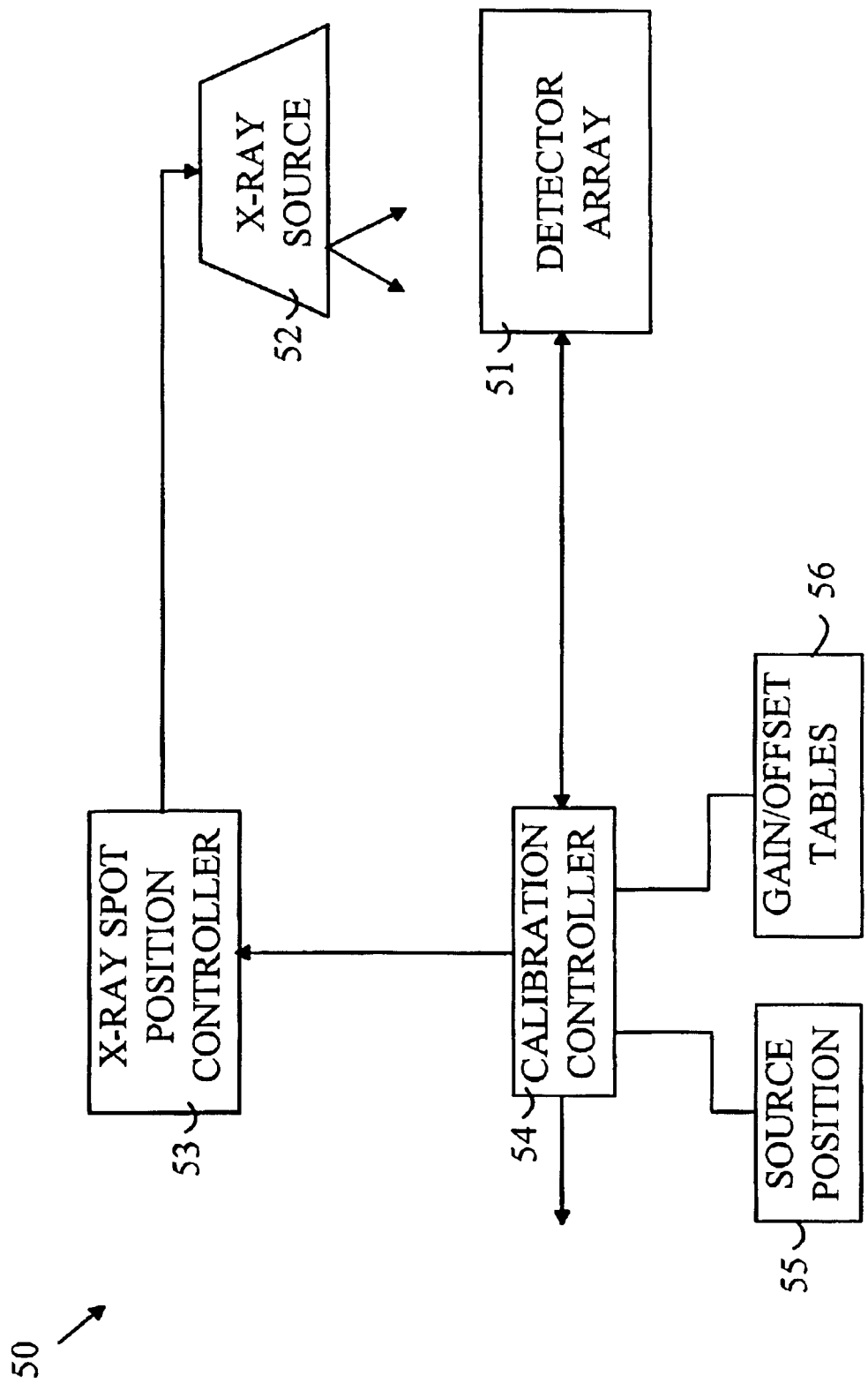
FIG. 2 is a schematic drawing of an imaging system 50 according to one embodiment of the present invention.

Refer now to FIG. 2, which is a schematic drawing of an imaging system 50 according to one embodiment of the present invention. Imaging system 50 utilizes a scanning x-ray source 52 to provide a point source of x-rays in which the location of the point source is controlled by a position controller 53 that is controlled by calibration controller 54. The x-ray source preferably varies the point source position over a two-dimensional area such that the object being scanned can be viewed from substantially different directions. However, embodiments in which the position is varied over a one-dimensional linear path can also be advantageously utilized. In addition, embodiments in which the point source remains fixed in space and the detector array is moved relative to the point source can also be constructed.

A detector array 51 measures the x-rays that pass through the object being imaged. The detector array preferably includes a plurality of individual "pixel" detectors, each detector measuring the x-rays received from a small solid angle relative to the point source. Arrays of detectors for measuring x-ray images are known to the art, and hence, detector array 51 will not be discussed in detail here. For the purposes of this discussion, it is sufficient to note that detector array 51 can be readout by calibration controller 54.

In the embodiment shown in FIG. 2, the location of the point source relative to a reference point on the detector array is stored in a memory 55 connected to calibration controller 54. Information specifying the location of each pixel in detector array 51 relative to this reference point is also stored in calibration controller 54. This information can be represented as locations within a single coordinate system or as a coordinate transform between the respective coordinate systems used for the detector array and the point source addressing. Hence, for any given relative point source position, calibration controller 54 can compute the angle between the normal to the pixel array and the ray from the point source to each pixel in detector array 51, i.e., the angle $\theta$ discussed above.

The data stored in tables 56 is generated by measuring the output of detector array 51 for at least two different relative source positions and then determining the constants shown in Eq. (1) for each pixel in the array. Since data fitting algorithms suited to making this determination are well known in the art, the details of such algorithms will not be discussed in detail here.

Figure 3:
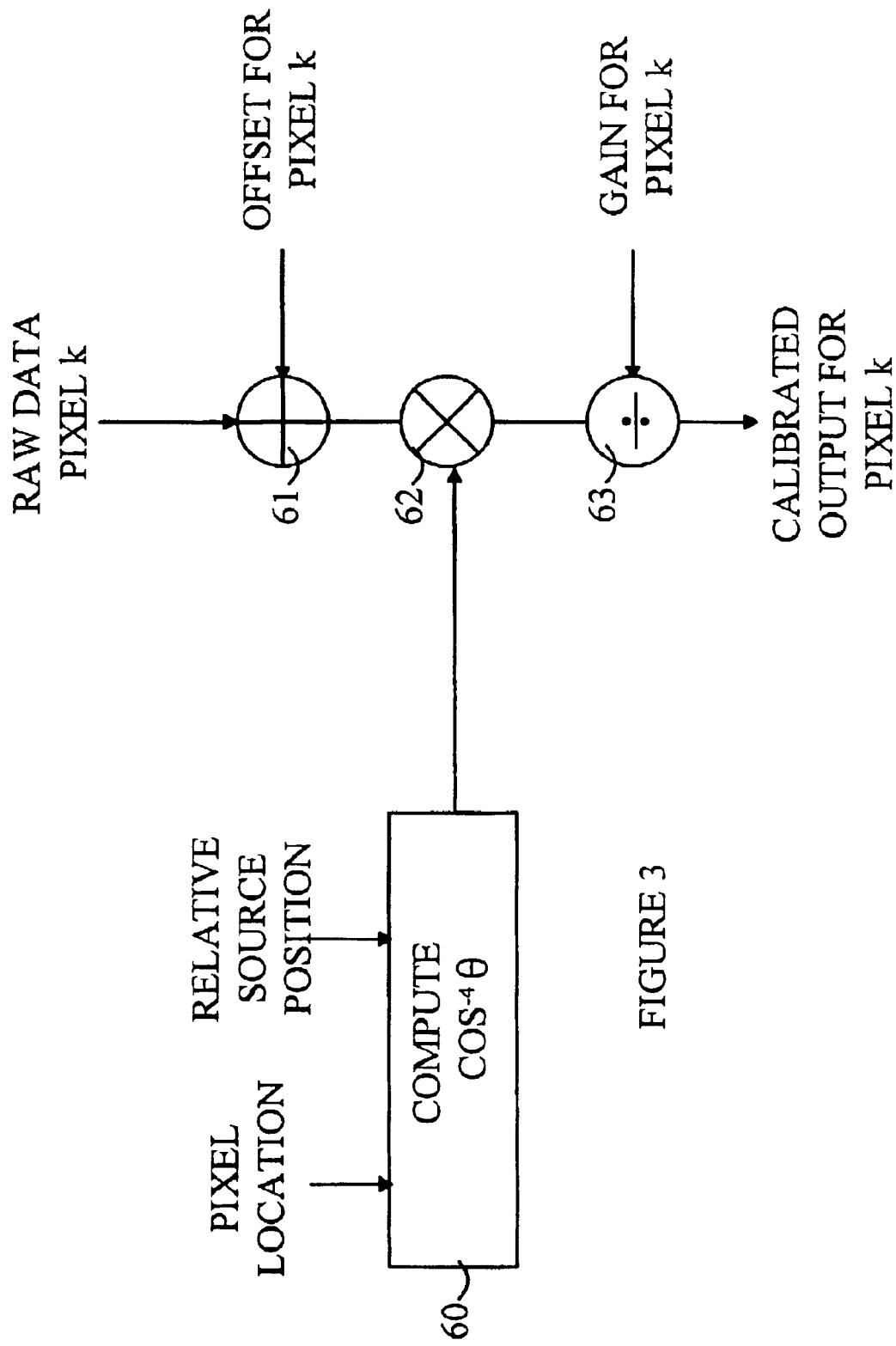
FIG. 3 is a schematic drawing of one embodiment of a pipelined processor for correcting the image data.

In one preferred embodiment, the data from the detector array is corrected for the variations in $\theta$, gain and offset via a pipelined processor that corrects each measured intensity value as the measured value is received from the detector array. Refer now to FIG. 3, which is a schematic drawing of one embodiment of a pipelined processor for correcting the image data. When the data for a pixel is read out of the detector array, the current relative position of the point source, and the detector array is combined with the location of the pixel in question within the array to determine cosine$^{-4}\theta$ as shown at 60. The pixel intensity is input to a subtraction circuit 61 that subtracts the offset stored in the tables shown at 56 in FIG. 2 for the current pixel. The offset corrected data is then corrected for the cosine $\theta$ dependence by multiplier 62. Finally, the result from multiplier 62 is divided by the gain using divider 63 to generate a corrected pixel value.

The above-described embodiments of the present invention have been described in terms of an array of detectors. However, it should be noted that this array of x-ray detectors can include sub-arrays of x-ray detectors. For example, the imaging plane may be populated with many CCD imagers, which are multi-pixel arrays in themselves. It should also be noted that an imaging array that utilizes a number of sub-arrays in which the individual sub-arrays lie in different planes might also be utilized.

Various modifications to the present invention will become apparent to those skilled in the art from the foregoing description and accompanying drawings. Accordingly, the present invention is to be limited solely by the scope of the following claims.

What is claimed is:

1. An imaging system comprising:

an x-ray detection array comprising a plurality of x-ray detectors, each x-ray detector generating a signal indicative of the x-ray energy absorbed by said x-ray detector and being located at a location in said detection array;

a point x-ray source that moves relative to said detection array, each x-ray detector subtending at said point source a solid angle that depends on a relative position of said point source and said detection array and on said location of said detector in said detection array; and a controller, wherein said signal generated by each x-ray detector depends on a calibration parameter that is independent of said solid angle subtended by that x-ray detector at said point source, wherein said controller comprises a memory that stores a table of calibration values that determines said calibration parameter for each of said x-ray detectors, and wherein said controller corrects said signals generated by said x-ray detectors for variations in said solid angle subtended by each of said x-ray detectors and for variations in said calibration parameter.

2. The image system of claim 1 wherein said controller further comprises a processor that determines said calibration values by measuring said signal from each of said x-ray detectors for two different relative positions of said x-ray source and said detection array.

3. The imaging system of claim 1 wherein said calibration parameter defines a gain for that x-ray detector.

4. The imaging system of claim 1 wherein said calibration parameter defines an offset value for that x-ray detector.

5. The imaging system of claim 1 wherein said controller comprises a pipelined processor for correcting said signals generated by said x-ray detectors as said signals are readout of said x-ray detection array.

6. A method for correcting image data generated by an x-ray detection array comprising a plurality of x-ray detectors when an object is imaged by a point x-ray source that moves relative to said detection array, each of said x-ray detectors subtending at said point source a solid angle that depends on a relative position of said point source and said detection array and on said location of said detector in said detection array, each x-ray generating a signal indicative of the x-ray energy absorbed by that x-ray detector, wherein said signal generated by each x-ray detector depends on a calibration parameter that is independent of said solid angle subtended by that x-ray detector at said point source, said method comprising:

storing a table of calibration values that determines said calibration parameter for each of said x-ray detectors; and correcting said signals generated by said x-ray detectors for variations in said solid angle subtended by each of said x-ray detectors and for variations in said calibration parameter.

7. The method of claim 6 further comprising determining said calibration parameters by measuring said signal from each of said x-ray detectors for two different relative positions of said x-ray source and said detection array.

8. The method of claim 6 wherein said calibration parameter defines a gain for that x-ray detector.

9. The method of claim 6 wherein said calibration parameter defines an offset value for that x-ray detector.

* * * * *